(12) United States Patent
Nobles

(10) Patent No.: US 6,248,121 B1
(45) Date of Patent: *Jun. 19, 2001

(54) BLOOD VESSEL OCCLUSION DEVICE

(75) Inventor: Anthony A. Nobles, Fountain Valley, CA (US)

(73) Assignee: Cardio Medical Solutions, Inc., Fountain Valley, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/121,443

(22) Filed: Jul. 23, 1998

Related U.S. Application Data

(60) Provisional application No. 60/075,024, filed on Feb. 18, 1998.

(51) Int. Cl.[7] .................................................. A61M 29/00
(52) U.S. Cl. ............................................................ 606/194
(58) Field of Search ................................... 606/194, 195, 606/108, 192; 604/96, 97, 99, 100, 102, 915, 104

(56) References Cited

U.S. PATENT DOCUMENTS

Re. 35,352    10/1996    Peters .

(List continued on next page.)

FOREIGN PATENT DOCUMENTS

28075/89    9/1991    (AU) .

(List continued on next page.)

OTHER PUBLICATIONS

U.S. patent application No. 09/080,823, filed on May 18, 1998, entitled "Device and Method for Partially Occluding Blood Vessels Using Flow–Through Balloon" by Anthony Nobles.

Primary Examiner—Jeffrey A. Smith
Assistant Examiner—Eduardo C. Robert
(74) Attorney, Agent, or Firm—Knobbe, Martens, Olson & Bear, LLP

(57) ABSTRACT

A direct-access device with a thin-profile balloon member is used to occlude a blood vessel. The device is ideally suited for occluding a patient's aorta during stopped-heart cardiac procedures. The device comprises a flexible, thin-profile balloon member which forms a balloon in combination with a tubular member, which inflates the thin-profile balloon member. Together, the balloon member and tubular member occlude a blood vessel. The balloon member is attached near the distal end of the tubular member. The width of the balloon member's outer peripheral contact area, which contacts the inner wall of the blood vessel, is substantially narrower than the balloon member's diameter. The balloon member is made of a low compliance material which prevents the balloon member from expanding by more than 40% radially and 50% longitudinally after the balloon member is initially inflated under ambient pressure to its normal, unstretched shape. The balloon member comprises at least one pair of internal ribs which support the structure of the balloon member and prevent the balloon member from expanding longitudinally by more than 50%. The balloon member with internal ribs may be formed by dipping a mandrel, with grooves or channels formed therein, a number of times into liquid polyethylene, polyurethane or other similar material. The tubular member comprises a first lumen which carries blood between the patient and an external medical device. Another lumen is used to inflate and deflate the thin profile balloon member. Other lumens are used to measure blood pressure, introduce cardioplegia solution or drugs, and/or compensate for over-inflation of the balloon member. The tubular member is preferably bent near the distal end to allow the balloon member to be directly introduced into the blood vessel.

43 Claims, 12 Drawing Sheets

U.S. PATENT DOCUMENTS

| | | | |
|---|---|---|---|
| 2,473,742 | * | 6/1949 | Auzin ................................. 604/100 |
| 3,292,627 | * | 12/1966 | Harautuneian ..................... 604/100 |
| 3,394,705 | | 7/1968 | Abramson . |
| 4,119,100 | | 10/1978 | Rickett . |
| 4,573,966 | | 3/1986 | Weikl et al. . |
| 4,734,094 | | 3/1988 | Jacob et al. . |
| 4,771,776 | | 9/1988 | Powell et al. . |
| 4,796,629 | * | 1/1989 | Grayzel ................................ 604/96 |
| 4,861,330 | | 8/1989 | Voss . |
| 4,898,168 | | 2/1990 | Yule . |
| 4,932,956 | | 6/1990 | Reddy et al. . |
| 4,983,116 | | 1/1991 | Koga . |
| 5,090,958 | | 2/1992 | Sahota . |
| 5,106,363 | * | 4/1992 | Nobuyoshi ......................... 606/194 |
| 5,116,305 | | 5/1992 | Milder et al. . |
| 5,286,259 | * | 2/1994 | Ganguly et al. ................... 606/194 |
| 5,308,323 | * | 5/1994 | Sogawa et al. ..................... 606/192 |
| 5,370,618 | | 12/1994 | Leonhardt . |
| 5,382,261 | | 1/1995 | Palmaz . |
| 5,383,854 | | 1/1995 | Safar et al. . |
| 5,425,708 | | 6/1995 | Nasu . |
| 5,458,574 | | 10/1995 | Machold et al. . |
| 5,522,961 | | 6/1996 | Leonhardt . |
| 5,558,644 | | 9/1996 | Boyd et al. . |
| 5,591,195 | | 1/1997 | Taheri et al. . |
| 5,681,296 | * | 10/1997 | Ishida ................................... 604/96 |
| 5,688,245 | * | 11/1997 | Runge ................................... 604/96 |
| 5,695,468 | * | 12/1997 | Lafontaine et al. ................ 606/192 |
| 5,795,325 | * | 8/1998 | Valley et al. ...................... 604/100 |
| 5,797,948 | * | 8/1998 | Dunham .............................. 606/194 |
| 5,868,708 | * | 2/1999 | Hart et al. ........................... 604/96 |
| 5,928,192 | * | 7/1999 | Maahs ................................. 604/96 |

FOREIGN PATENT DOCUMENTS

| | | |
|---|---|---|
| 29 01 701 | 7/1980 | (DE) . |
| 0894 475 A1 | 2/1999 | (EP) . |

* cited by examiner

BLOOD VESSEL OCCLUSION DEVICE

PRIORITY CLAIM

This application claims the benefit of provisional application No. 60,075,024 filed Feb. 18, 1998.

BACKGROUND OF THE INVENTION

1. Field of the Invention

The present invention relates generally to occlusion devices and methods of use thereof. More specifically, the present invention relates to balloon occlusion devices for performing cardiac bypass or other vascular procedures.

2. Brief Description of the Related Art

Coronary artery diseases are often caused by atherosclerosis or narrowing of the small arteries between the aorta and the heart muscles. There are several ways to provide blood blow around occluded segments of arteries or veins, however, the known methods commonly cause a large amount of trauma to the patient. One method is to perform an "open heart surgery," which involves cracking open the chest and exposing the heart and treating the vessel directly. However, the large incision and surgically cut sternum take a long time to heal.

In the bypass operation, a section of the saphenous vein, or a suitable substitute, is grafted, usually between the ascending aorta just above the heart and one or more of the coronary arteries beyond the points of blockage. The bypass operation is performed with the patient connected to a heart-lung machine and the heart is stopped. Because the heart is stopped, the heart-lung bypass can damage blood cells. Additionally, the patient's internal body temperature is reduced while on a heart-lung bypass to reduce basil metabolism and then the body temperature is increased to normal when the procedure is over. This thermal change to a person's body can cause damage to the intestinal track as well as causing additional stress to the patient.

If the patient is not placed on a heart-lung bypass, the aorta is typically partially clamped along its axis to create an area of blood stasis and a small channel for blood flow. However, clamping the aorta can cause injury to the aorta and can also cause plaque formations to break off into the blood stream and cause severe disorders such as strokes and emboli.

Sometimes, occlusion balloons are inserted through the femoral artery up to the blood vessel to be occluded. Both clamps and existing occlusion devices commonly cause damage to the internal blood vessel walls and they introduce plaque into the patient's blood stream. Existing balloons are also likely to move longitudinally along the catheter while in the blood vessel, and thus are likely to move into the heart or interfere with blood flow.

SUMMARY OF THE INVENTION

The present invention relates to a direct-access device with a balloon for occluding blood vessels, and methods of use thereof. The invention also relates generally to the design and manufacturing of this occlusion device. The occlusion device is ideally suited for occluding a patient's aorta during stopped-heart cardiac procedures.

A preferred embodiment of the present device comprises a flexible balloon member which is attached to the exterior of a tubular member to form an inflatable balloon. The tubular member includes an inflation lumen which can be used to inflate and deflate the thin-profile balloon. Together, the balloon member and tubular member occlude a blood vessel. The balloon member is preferably attached near the distal end of the tubular member. The width of the outer peripheral contact area of the balloon member, which comes in contact with the inner wall of the blood vessel, is substantially narrower than the balloon member's diameter. The contact area between the balloon member and the inner blood vessel wall is thus reduced over prior designs.

The balloon member is preferably made of a low compliance material, which limits the expansion of the balloon member to expanding 1% to 40% radially and 1% to 50% longitudinally after the balloon member is initially inflated under ambient pressure to its normal, unstretched shape. In one embodiment, the low compliance material limits the expansion of the balloon member to expanding 10% to 33% radially and 10% to 40% longitudinally. In one embodiment, the low compliance material comprises polyurethane.

In addition to the inflation lumen, the tubular member preferably comprises a blood flow lumen which carries blood between the patient and an external medical device, such as a heart-lung machine. The tubular member preferably has other lumens to measure blood pressure and introduce a cardioplegia solution and/or drugs. In one embodiment, the tubular member is bent near the distal end to allow the balloon member to conveniently be directly introduced into and positioned within the blood vessel.

A significant advantage of the present device is that the inflated balloon member has a thin profile at its periphery. In a preferred embodiment, the balloon member produces a longitudinal contact distance which is less than 50% of (and preferably 20–30% of) the inner diameter of the blood vessel. Thus, the thin-profile balloon member contacts only a narrow segment of the blood vessel when the balloon member is inflated. Because the surface area of contact is reduced, the potential damage to the blood vessel commonly caused by such contact is also reduced. Another benefit of using a thin-profile balloon member is that the balloon member is less likely to move longitudinally along the catheter while in the blood vessel, and thus less likely to move into the heart or interfere with the device's blood flow port.

Another substantial advantage of the present device is that it can be used to occlude the aorta without the need for clamps, and thus reduces the likelihood of plaque being introduced into the blood stream.

Another important advantage results from the limited compliance of the balloon member. The limited compliance of the balloon member reduces longitudinal stretching and maintains a small peripheral surface area which comes in contact with the internal blood vessel wall. This prevents the balloon member from blocking the distal end of the tubular member or the opening of a branching blood vessel, such as the innominate artery. The limited compliance also limits radial stretching, and thus reduces potential damage to the blood vessel wall. In addition, the limited compliance reduces the likelihood of dissections and breakoffs of the inflatable balloon member, and reduces the risk of the balloon bursting.

If the balloon is inserted in the aorta, another advantage of the thin-profile of the balloon is that it allows the physician to move the balloon closer to the innominate artery (brachiocephalic artery). This creates more working space in the aorta for anastomosis.

In one embodiment, the balloon member comprises at least one pair of internal ribs which support the structure of the balloon member (maintain its thin profile) and prevent the balloon member from expanding by more than 1% to 50% after the balloon member is initially inflated. In one embodiment, the internal ribs limit the longitudinal expansion of the balloon member even further than the limited compliance material. These internal ribs interconnect the proximal and distal walls of the balloon member. In one configuration of balloon member, the ribs overlap one another and are bonded together. The balloon member with internal ribs may be formed by dipping a mandrel, with grooves or channels formed therein, a number of times into liquid polyethylene, polyurethane or other material with similar properties. In other embodiments of the invention, the internal ribs feature may be used to limit or control the expansion of other types of occlusion balloons, such as angioplasty balloons.

In another configuration, the balloon member comprises at least one indent or bump along the peripheral edge of the balloon member. These indents or bumps help to maintain the position of the balloon member within the blood vessel, prevent the balloon member from slipping, and reduce the contact area between the balloon and the internal wall of the blood vessel.

DETAILED DESCRIPTION OF THE PREFERRED EMBODIMENTS

Figure 1:
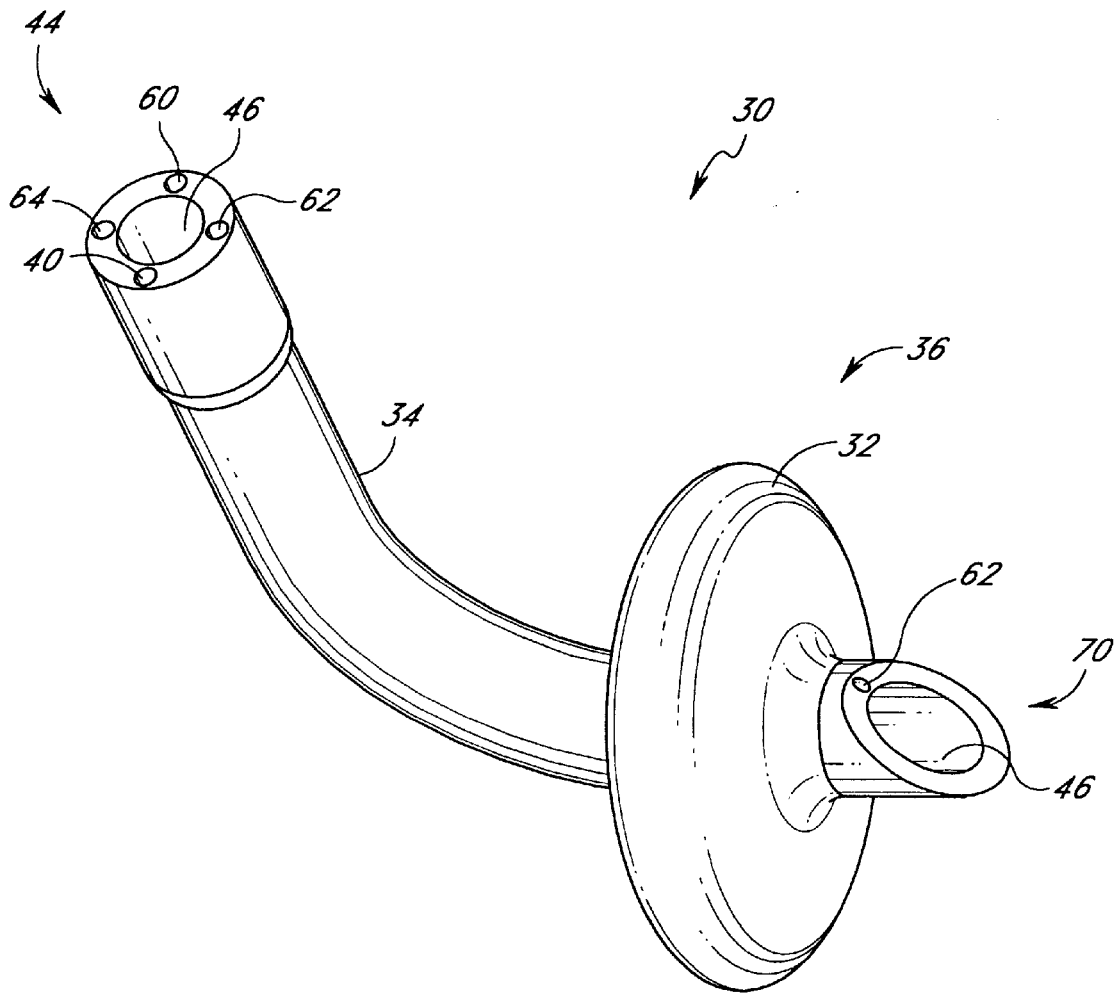
FIG. 1 is a perspective view of a direct-access blood vessel occlusion device in accordance with the invention, with the balloon of the device shown in an inflated state.

The present invention provides a direct-access blood vessel occlusion device 30 ideally suited for use during a stopped-heart cardiac procedure. In a preferred embodiment, as depicted by FIGS. 1–5, the device 30 comprises a flexible balloon member 32 which is attached to the outer surface of a multi-lumen tube 34 to form a balloon 36. The balloon 36 may be inflated and deflated using an inflation lumen 40 which extends axially from a proximal end 44 of the tube to port 40' within the interior of the balloon 36. A main lumen or blood flow lumen 46 extends axially through the center of the tube 34 and is used to carry blood between the patient's circulatory system and a heart-lung machine (not shown). In a preferred configuration, a bend (preferably ninety degrees) is formed in the multi-lumen tube 34 proximal to the balloon 36 to allow the balloon 36 to easily be directly introduced into, and positioned within, the blood vessel to be occluded. In another configuration (ideally suited for occluding the superior vena cava), the multi-lumen tube 34 is straight without a bend.

Figure 6:
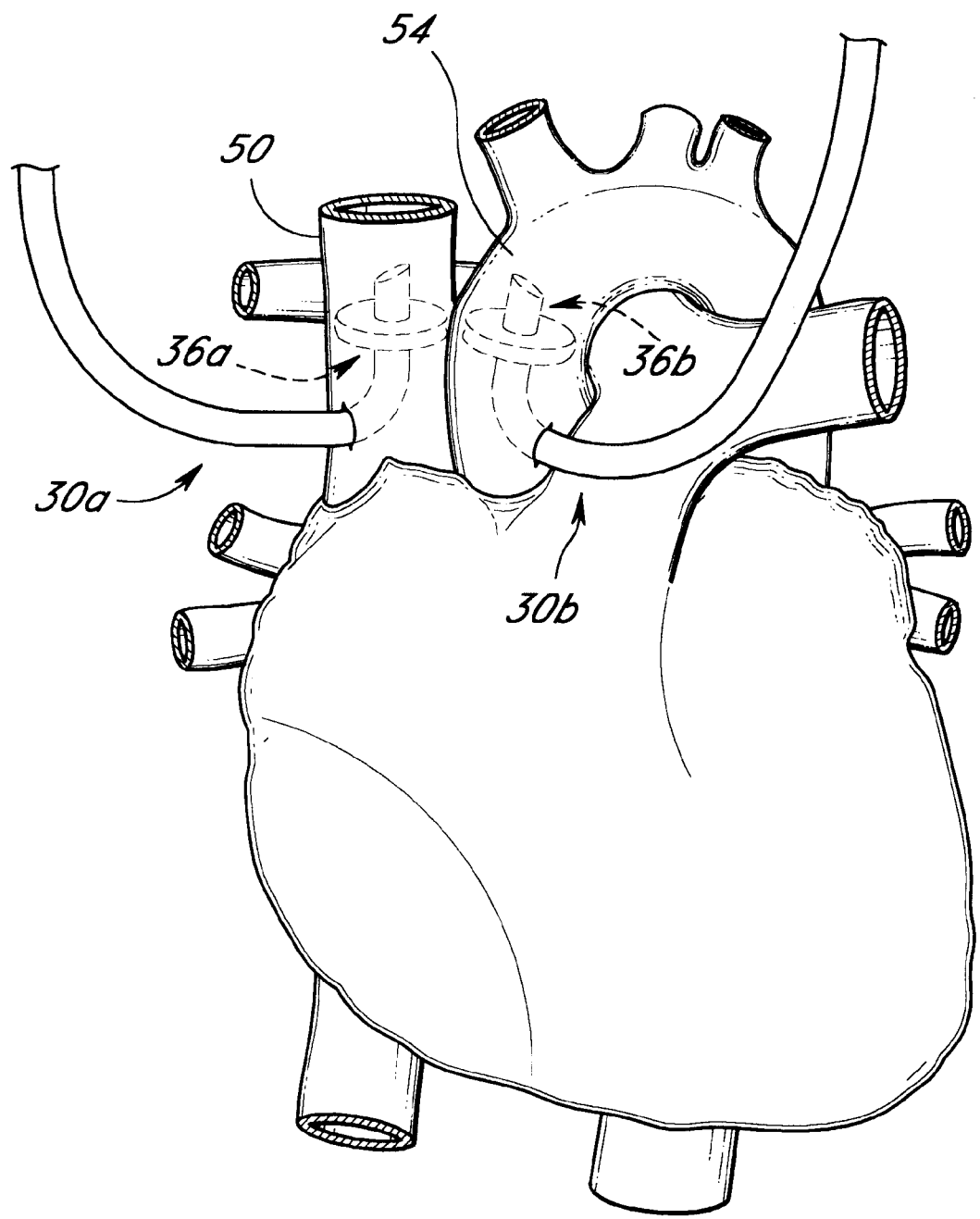
FIG. 6 illustrates how two of the occlusion devices may be used to achieve a state of cardiopulmonary bypass.

FIG. 6 illustrates how two such devices may be used to achieve cardiopulmonary bypass, such as during an aorto-coronary bypass procedure. For convenience, the reference characters "A" and "B" are appended to the FIG. 6 reference numbers to distinguish between the two devices. The first device 30A is used to occlude and draw blood from the patient's superior vena cava 50. A conventional non-occluding canula may alternatively be used for this purpose, in which case cardiopulmonary bypass is achieved without occluding the vena cava 50. The blood that is withdrawn using the first device 30a is passed through a heart-lung machine (not shown) for re-oxygenation. The second device 30B is used to occlude, and to reintroduce oxygenated blood into, the patient's aorta 54. The procedure by which the devices 30A, 30B are introduced into the blood vessels and used to achieve cardiopulmonary bypass is described below.

Figure 2:
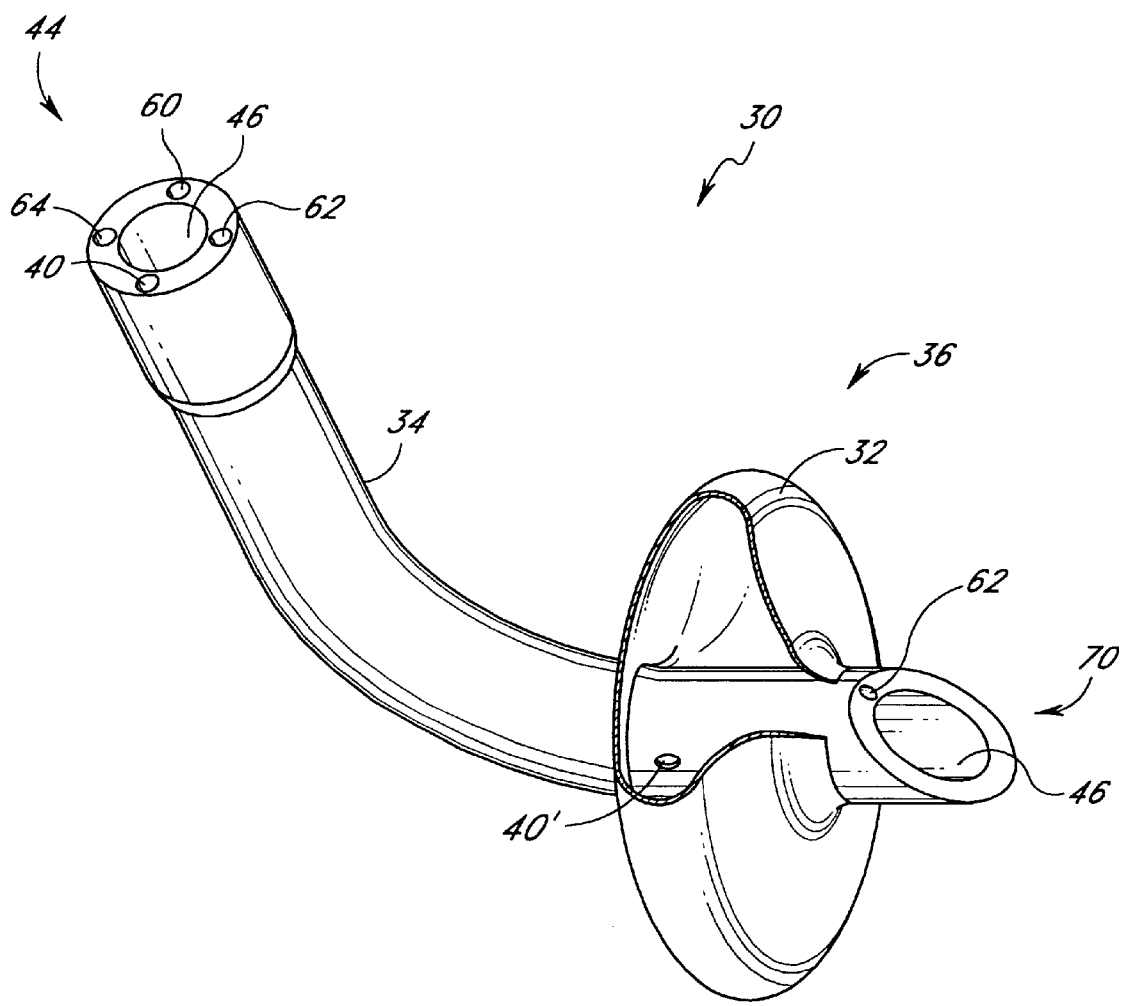
FIG. 2 is a partially cut-away perspective view of the occlusion device of FIG. 1.

An important feature of the device 30 is that the inflated balloon 36 has a thin profile at its periphery, and thus contacts only a narrow segment of the blood vessel (vena cava or aorta) when the balloon is inflated. By way of background, existing balloon occlusion devices commonly produce a longitudinal contact distance (the longitudinal distance over which the inflated balloon contacts the inner wall of the blood vessel) which exceeds the inner diameter of the blood vessel. In contrast, the device 30 described herein produces a longitudinal contact distance which is less than 50% (and preferably 20–30%) of the inner diameter of the blood vessel. Because the area of contact is reduced, the potential damage commonly caused by such contact is also reduced. The balloon member 32 is preferably substantially disk- shaped as shown in FIGS. 1 and 2. Alternatively, the shape of the balloon member 32 may resemble a spinning top. The shape of the balloon member 32 may be designed in various configuration, but the width of the outer peripheral contact area, which contacts the inner wall of the blood vessel, remains less than 50% (and preferably 20–30%) of the inner diameter of the blood vessel.

Another benefit of using a thin-profile balloon is that the balloon is less likely to move longitudinally along the tube 34 (or catheter) while in the blood vessel, and thus less likely to move into the heart or interfere with the device's blood flow port.

Figure 5:
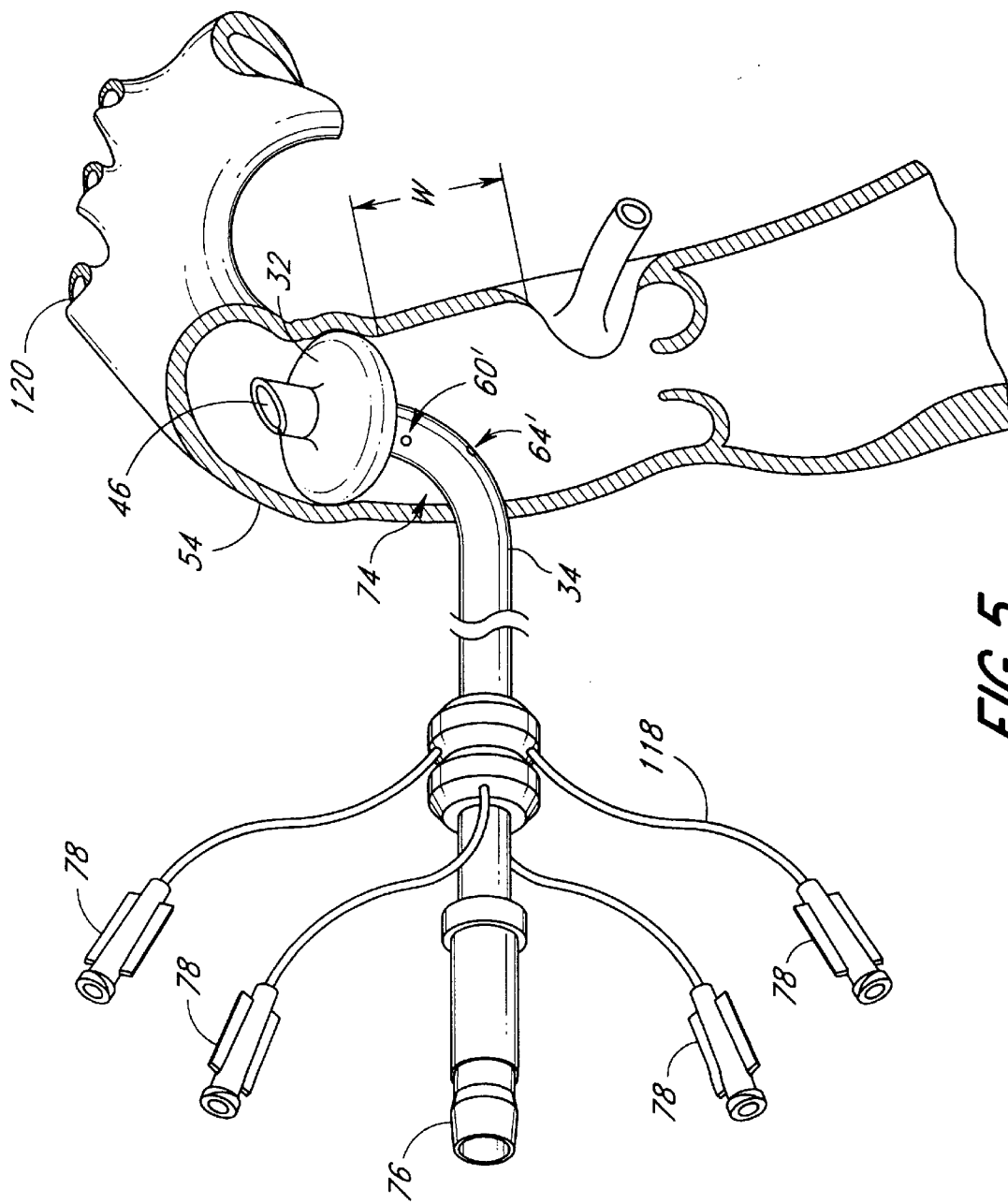
FIG. 5 illustrates the use of the occlusion device to occlude the aorta of a patient, and illustrates one type of connector that may be provided at the proximal end of the device.

If the balloon 36B is inserted in the aorta 54, another advantage is the thin-profile of the balloon 36B allows the physician to move the balloon 36B closer to the innominate artery (brachiocephalic artery) 120, and thus create more working space (labelled 'W' in FIG. 5) in the aorta 54 for anastomosis. This is shown in FIG. 5.

In another embodiment (not illustrated) of the invention, a longer segment of tube is provided distal to the bend, and two balloons 36 (both of the same general construction as in the single-balloon configuration) are spaced apart from one another along this tube segment. The two balloons are preferably fluidly coupled to a common inflation lumen of the tube 34. The spacing between the two balloons is sufficient to form a working area for performing an anastomosis between the two inflated balloons. The use of two balloons in this manner prevents blood from flowing in the region of the anastomosis site during the anastomosis procedure, as described generally in U.S. provisional application No. 60/046,977 filed May 19, 1997.

Figure 3:
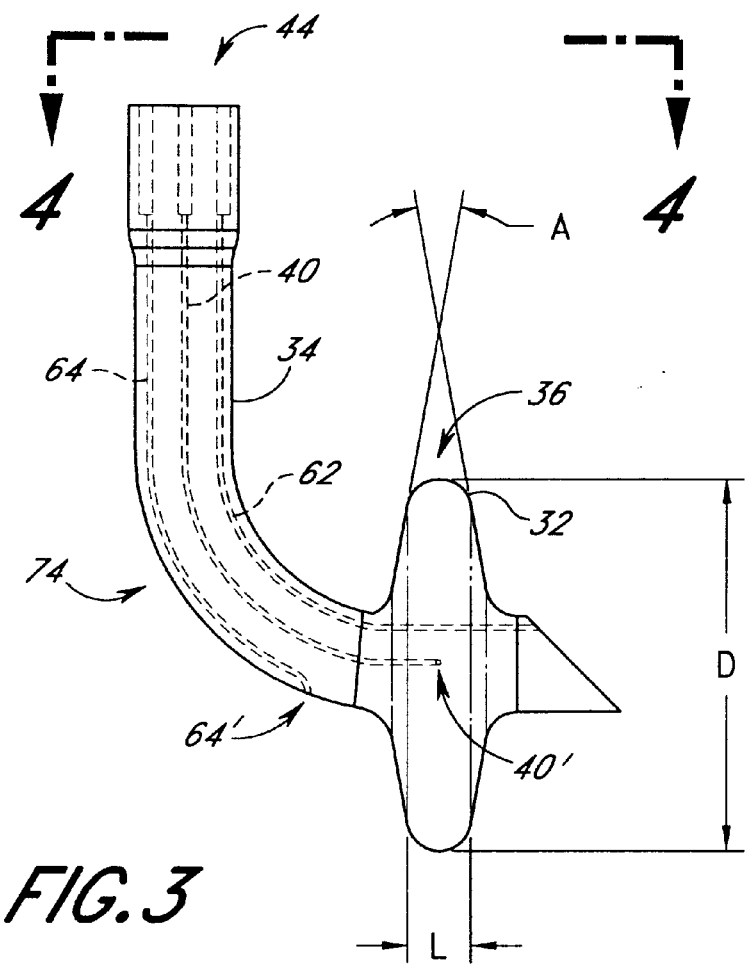
FIG. 3 is a side view of the occlusion device, with three of the device's five lumens shown in dashed lines.
Figure 4:
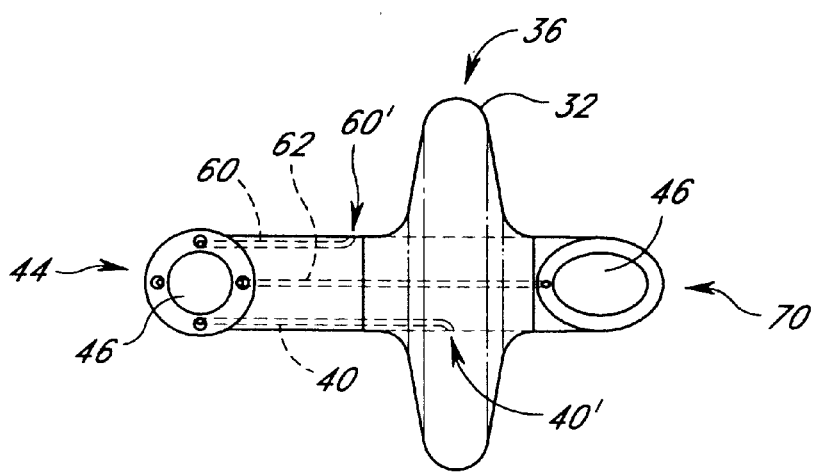
FIG. 4 is a top view of the occlusion device taken from the line 4—4 of FIG. 3, with three lumens shown in dashed lines.

The general construction of the device 30 will now be described in further detail with reference to FIGS. 1–5. As best shown by FIGS. 3 and 4, the multi-lumen tube 34 includes the blood flow lumen 46, the inflation lumen 40, a proximal blood pressure lumen 60, a distal blood pressure lumen 62, and a cardioplegia lumen 64. Each lumen extends axially from the proximal end 44 of the tube 34. The blood flow lumen 46 and the distal blood pressure lumen 62 extend to the tapered, distal end 70 of the tube 34. The proximal blood pressure lumen 60 and the cardioplegia lumen 64 extend to respective openings 60', 64' in the outer surface of the tube 34 proximal to the balloon 36. The inflation lumen 40 extends to an opening 40' which coincides in position with the interior of the balloon 36. A standard barbed fitting 76 is provided at the proximal end of the multi-lumen tube 34 to enable other tubes and connectors to be fluidly coupled to each of the five lumens.

In the embodiment illustrated in FIGS. 1–4, the proximal end 44 of the multi-lumen tube 34 is in the form of a female connector. The female connector enables the device 30 to be coupled to the heart-lung machine, pressure sensors, and injection valves via a single connection. In the embodiment shown in FIG. 5, the device 30 is instead provided with a standard barbed connector 76 for coupling the blood-flow lumen 46 to the heart-lung machine, and is provided with four standard valved luer fittings 78 for providing access to the smaller lumens 40, 60, 62, 64. Any of a variety of other types of connectors can be used.

Figure 14A:
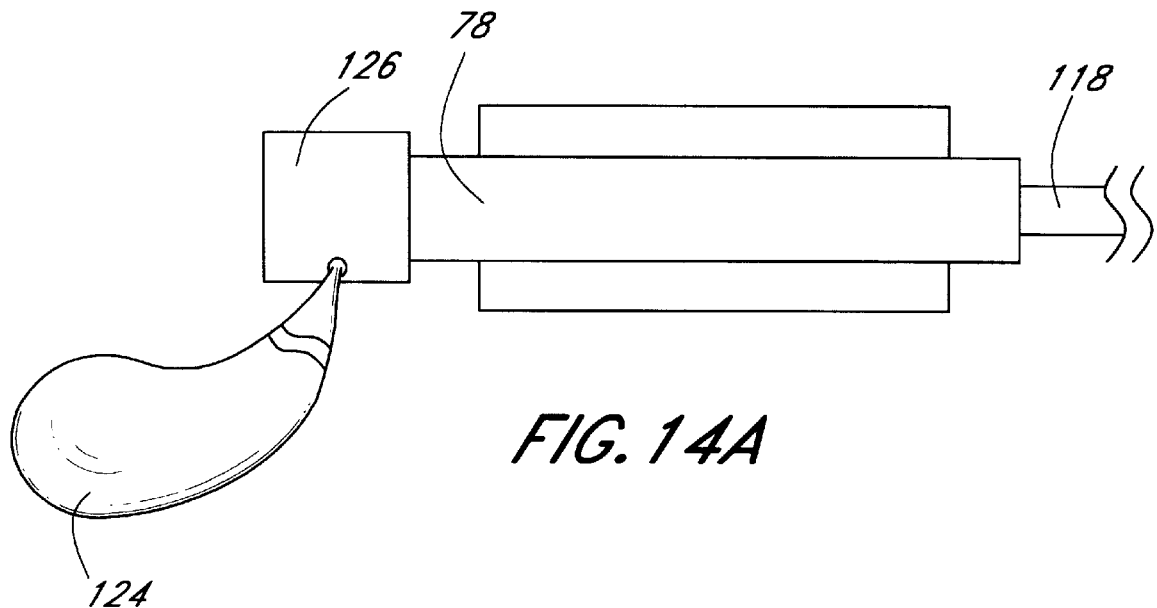
FIGS. 14A and 14B are side views of a flexible tube, similar to the tubes shown in FIG. 5, in fluid communication with an over-inflation balloon and a pressure sensor, respectively.

One or more of the lumens (or additional lumens) may, of course, be used for other purposes. For example, the inflation lumen 40 may serve an additional purpose: to prevent over-inflation of the occlusion balloon 36. In a preferred embodiment, the proximal end of the inflation lumen 40 is attached to a flexible tube 118, as shown in FIG. 5. The proximal end of the flexible tube 118 is attached to a luer fitting 78. An over-inflation 124 (FIG. 14A) is attached to a luer connector 126, which is attached to a luer fitting 78. A one-way, syringe-activated valve is built inside the luer connector 126. The over-inflation balloon 124 provides a space for sliding the distal part of the valve. In a preferred embodiment, the over-inflation balloon 124 is a 'Pilot' balloon made by Mallinckrodt Medical, Inc.

When the physician inserts a syringe into the luer fitting 78 and the valve to inflate the occlusion balloon 36, a component inside the valve moves distally to allow the syringe to insert the inflation fluid. If the physician pulls the inflation syringe out, the valve closes (the component inside moves proximally) and prevents the occlusion balloon 36 from losing its inflation. To deflate the balloon 36, the physician inserts the syringe into the valve and withdraws the fluid.

When the occlusion balloon 36 begins to inflate, there is no resistance on the balloon 36 as it expands, and there is no back pressure in the inflation lumen 40. But when the occlusion balloon 36 comes in contact with the inner walls of the blood vessel, the walls of the blood vessel create resistance on the expanding balloon 36. This creates back pressure in the inflation lumen 40, and the over-inflation check balloon 124 begins to inflate or bulge. This provides a direct signal to the physician that the inflated occlusion balloon 36 has contacted the internal walls of the blood vessel. The threshold pressure level needed to inflate the over-inflation balloon 124 may also be produced by attempts to inflate the balloon 36 beyond its maximum diameter, even though the balloon 36 may not be in contact with the vessel walls.

Figure 14B:
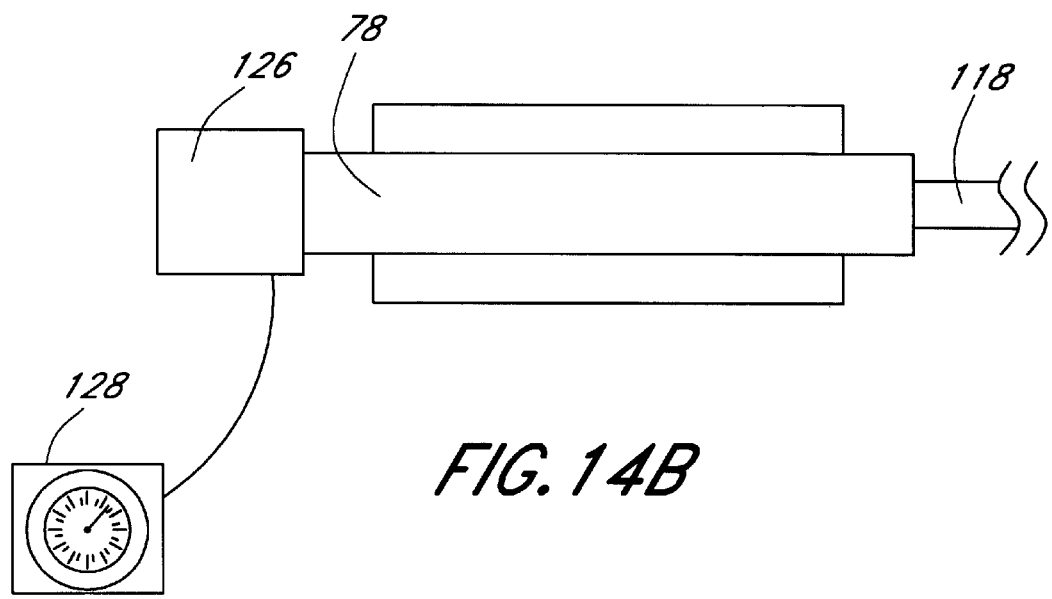

Alternatively, in addition to 124 an over-inflation balloon, some other pressure indicating device, such as a pressure meter 128 (FIG. 14B), may be used to indicate that the desired pressure level has been reached within the occlusion balloon 36. This pressure indicating device is fluidly coupled to the occlusion balloon 124 36.

Figure 15:
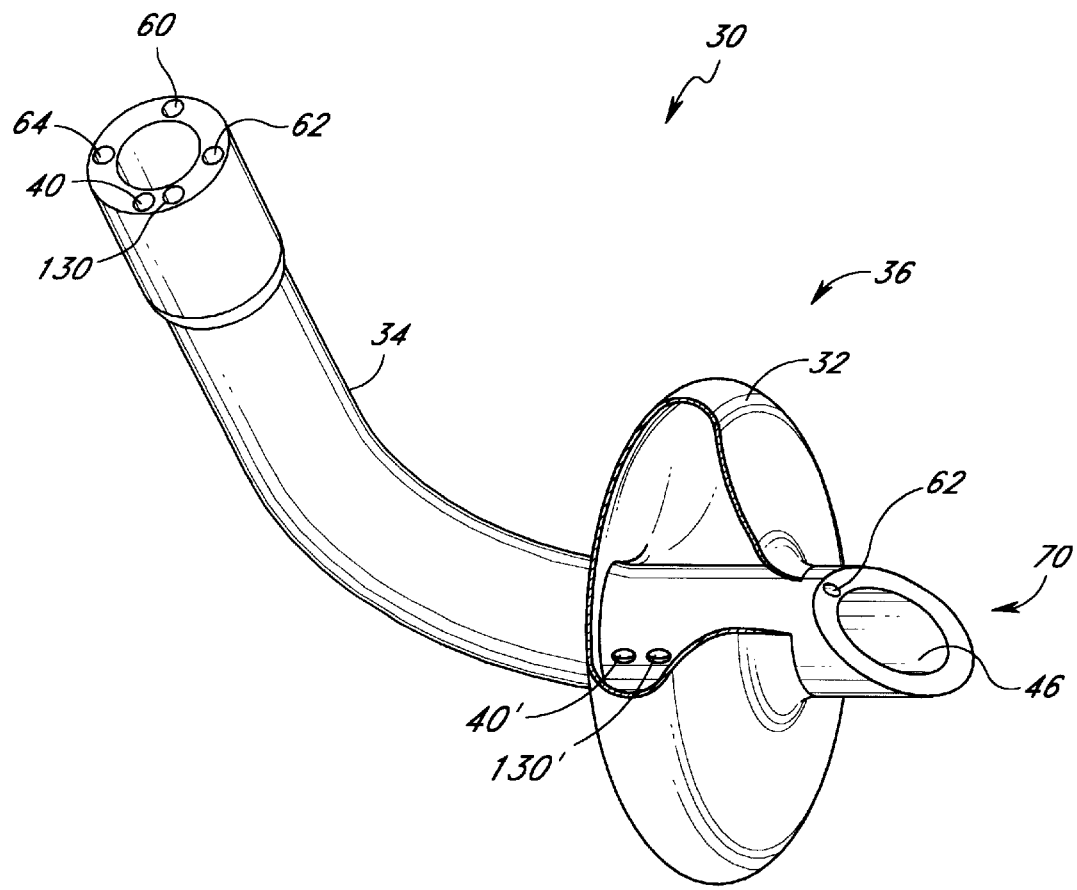
FIG. 15 is a partially cut-away perspective view of an occlusion device having an additional lumen which is in fluid communication with a pressure indicating device.

In another embodiment, the over-inflation check balloon or other pressure indicating device is coupled a to separate lumen 130 (FIG. 15) which runs parallel with the inflation lumen 40 along the tubular member 34 and extends to an opening which coincides in position with the interior of the balloon 36, similar to the opening 130 40'.

The thin-profile balloon member 32 is preferably formed from a limited compliance material, such as polyethylene, polyurethane, other polymers or any other material with similar properties. The balloon member 32 may comprise a mixture of materials. The material of the balloon member 32 is not fully compliant, like silicone or latex. The compliance of the material is preferably selected such that the balloon may stretch from 1% to 40% radially and from 1% to 50% longitudinally after it is initially inflated under ambient pressure to its normal, unstretched shape. In one embodiment, the low compliance material limits the expansion of the balloon member to expanding 10% to 33% radially and 10% to 40% longitudinally. During such expansion, the balloon 32 does not lose its overall shape. The width L (FIG. 3) of the balloon member 32 preferably never expands to be more than 50% (and preferably 20–30%) of the length of its diameter D. The use of a limited compliance material for this purpose reduces longitudinal stretching, and thus maintains a small peripheral surface area which contacts the internal wall of the blood vessel. The limited compliance also prevents the balloon member 32 from blocking the distal tip of the tube 34 or blocking the opening of a branching blood vessel, such as the innominate artery. The limited compliance also reduces the likelihood of dissections and breakoffs of the inflatable balloon 32.

The limited compliance material also reduces the risk of the balloon bursting, which is common for silicone or latex balloons. The balloon member 32 is made of a sufficiently thick material to be resistant to calcified lesions on the inner wall of the blood vessel.

With reference to FIG. 3, when the balloon 36 is inflated in free air, the diameter D of the balloon 36 is approximately three to five times the peripheral length or thickness L of the balloon. The diameter D of the inflated balloon 36 is preferably at least twice the diameter of the tube 34. In a preferred configuration, the angle A of the balloon is approximately 40 degrees.

The multi-lumen tube 34 is preferably formed of a semi-rigid, translucent material using a conventional extrusion process. Polyethylene may be used for this purpose, in which case the balloon member 32 may be bonded to the exterior of the tube 34 using a solvent bonding process. In a preferred embodiment, as best illustrated by the side view of FIG. 3, a ninety degree bend 74 is formed in the tube 34 proximal to the balloon 36. As depicted by FIG. 5, the curvature and position of this bend 74 are such that the straight, proximal portion of the tube 34 is perpendicular to the blood vessel 54 when the balloon 36 is properly oriented within the blood vessel. The bend 74 is preferably formed within the tubing 34 using a heat mandrel which is inserted within the blood flow lumen 46. In another configuration (ideally suited for occluding the superior vena cava), the multi-lumen tube 34 is straight without a bend.

The process by which the device 30 is used during a cardiac bypass procedure will now be described with reference to FIGS. 5 and 6. For purposes of this description, it will be assumed that the same type of device is used to occlude both the vena cava and the aorta.

Initially, the physician performs a thoracotomy, sternotomy or other procedure to obtain access to the patient's vena cava 50 and aorta 54. The physician then selects devices 30A, 30B having balloons 36A, 36B which correspond in diameter to the vena cava 50 and the aorta 54 (respectively) of the particular patient, and fluidly couples these devices 30a, 30b to the heart-lung machine and the various instruments to be used during the procedure. Incisions are then made in the vena cava 50 and the ascending aorta 54, and the distal ends of the devices 30a, 30b are advanced into the respective blood vessels to position the balloons. The balloons are maintained in an uninflated, collapsed state during the insertion process.

Once the devices 30A, 30B are positioned within the superior vena cava 50 and the ascending aorta 54, the heart-lung machine is activated such that blood is withdrawn from the vena cava 50 and perfused into the aorta 54. Each balloon 36A, 36B is then inflated by introducing an appropriate substance into the interior thereof via the respective inflation lumen 40 (FIGS. 3 and 4). The balloons 36A, 36B are preferably inflated with saline solution or any other suitable fluid. Locking syringes or syringes coupled to one-way valves may be used to inflate the balloons 36A, 36B.

The balloons 36A, 36B expand in diameter by about 1% to 40% (preferably 10% to 33%) from their initial inflated state during the inflation process. As illustrated by FIG. 5 for the aorta 54, the balloons 36A, 36B press outward against the inner walls of their respective blood vessels 50, 54 by a sufficient degree to cause the blood vessel walls to bulge outward slightly. Such bulging helps to maintain the inflated balloons in position.

Once the balloons 36A, 36B have been inflated, a cardioplegia solution is introduced into the heart to stop the heart from beating. The cardioplegia solution is preferably introduced via the cardioplegia lumen 64 (FIG. 3) of the aortic occlusion device 30b, although the cardioplegia lumen of the vena cava occlusion device 30a may additionally be used for this purpose. During the subsequent bypass or other cardiac procedure, the proximal and distal pressure lumens 60, 62 (FIGS. 3 and 4), may be used, along with one or more pressure sensors. to monitor the pressure on the proximal and distal sides of the inflated balloons 36A, 36B. These lumens 60, 62 may additionally or alternatively be used for other purposes, such as to introduce drugs into the heart and/or the circulatory system.

Figure 7:
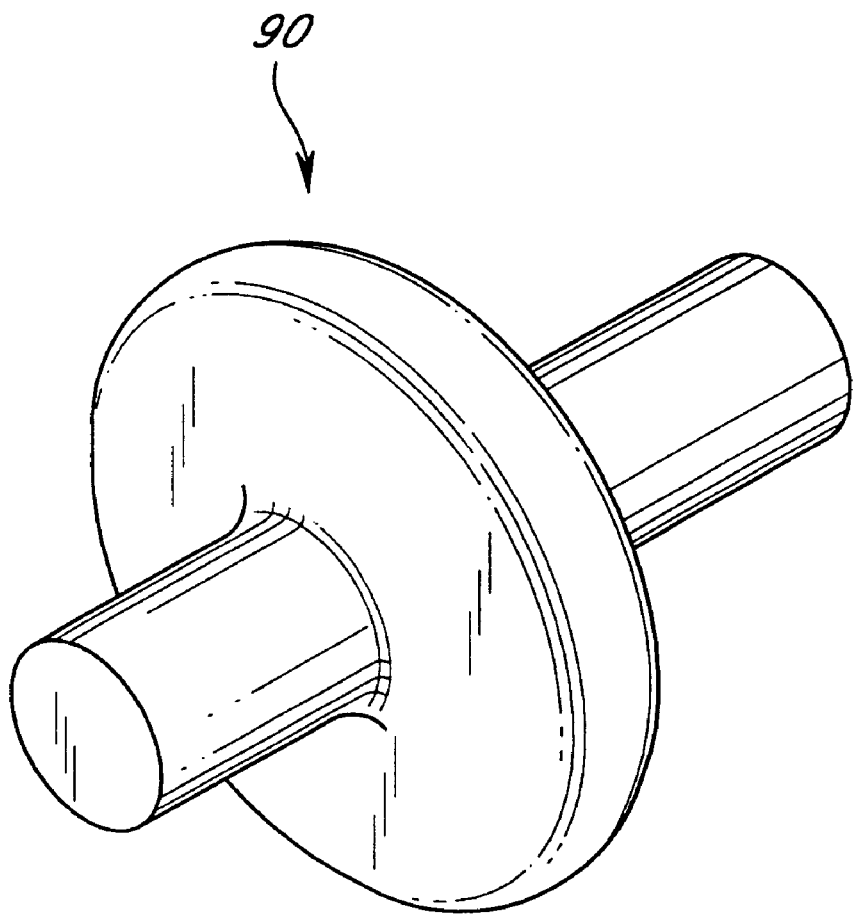
FIG. 7 is a perspective view of a mandrel that may be used to form the flexible balloon member of the occlusion device.

FIG. 7 illustrates a mandrel 90 which may be used to manufacture the thin-profile balloon members 32. The mandrel is preferably composed of 304 (or higher) stainless steel which is electropolished after machining. The diameter of the mandrel ranges from 1.0 to 1.5 cm in embodiments that are used for aortic occlusion. In one preferred embodiment, the diameter is equal to 1.102 cm, and in another preferred embodiment, the diameter is equal to 1.416 cm. During the manufacturing process, the mandrel 90 is appropriately dipped in a liquid polyethylene, polyurethane or other solution a sufficient number of times to produce a wall thickness of approximately 0.4 mils to 0.7 mils (where 1 mil=0.001 inches). The balloon member 32 is subsequently removed from the mandrel, and the tubular segments (not shown) which extend away from balloon portion in opposite directions are trimmed away. An appropriate powder may be applied to the balloon material to prevent the balloon walls from sticking together. Finally, the balloon member 32 is positioned over and bonded to the multi-lumen tube 34.

Figure 8:
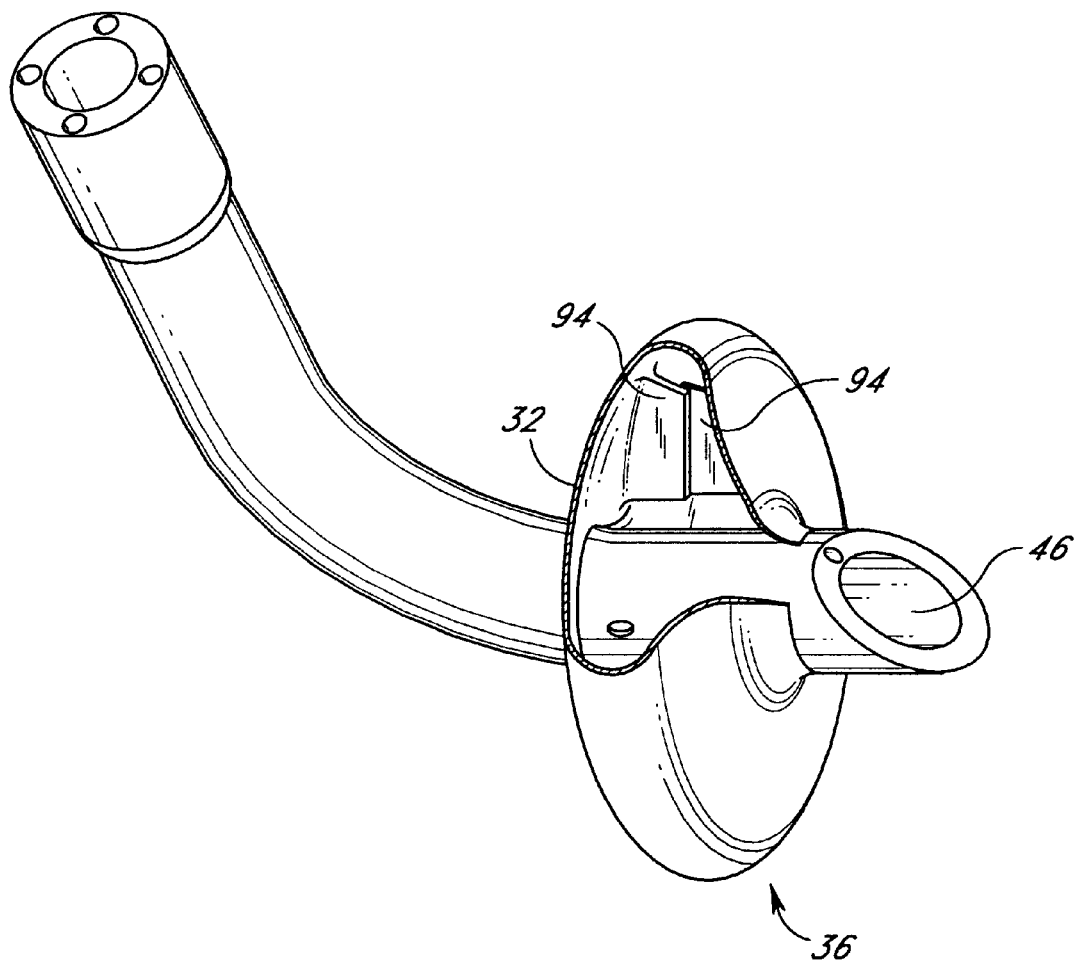
FIG. 8 is a partially cut-away perspective view of an alternative embodiment of the occlusion device, wherein internal ribs are provided within the balloon member to limit the longitudinal expansion of the balloon.

An optional feature of the balloon member 32 will now be described with reference to FIGS. 8–12. As illustrated by FIG. 8, the balloon member 32 may be provided with pairs of internal ribs 94 (one pair visible in FIG. 8) that interconnect the proximal and distal walls of the balloon. The use of such ribs 94 impedes the longitudinal expansion of the balloon 36 during inflation, and thus helps to maintain the thin profile of the balloon 36. In one embodiment, the internal ribs limit the longitudinal expansion of the balloon 36 even further than the limited compliance material. For example, if the limited compliance material prevents the balloon 36 from expanding longitudinally by more than 50%, the internal ribs may further limit longitudinal expansion up to only 10%. In the embodiment shown in FIG. 8, the two ribs 94 that are visible overlap one another and are bonded together. At least three pairs of attached ribs of the type shown in FIG. 8 are preferably provided within the balloon member 32, with the pairs spaced at equal angular intervals.

In other embodiments of the invention, the internal ribs feature may be used to limit or control the expansion of other types of occlusion balloons, such as angioplasty balloons.

Figure 9:
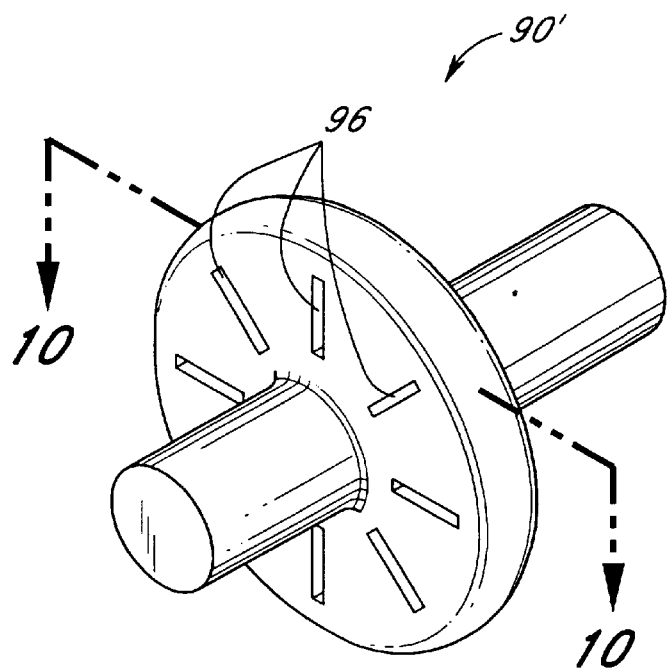
FIG. 9 is a perspective view of a mandrel which may be used to form a balloon member of the type shown in FIG. 8.
Figure 10:
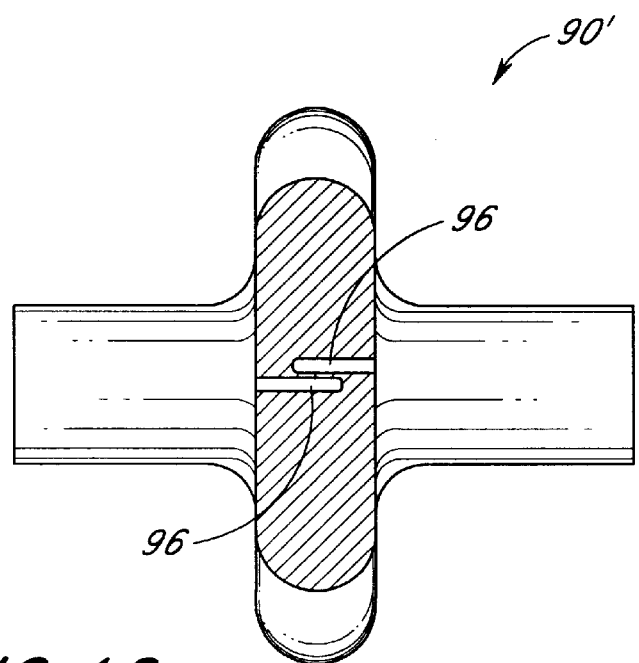
FIG. 10 is a cross sectional view taken along the line 10—10 of FIG. 9.

FIGS. 9 and 10 illustrate one embodiment of a mandrel 90' that can be used to form a balloon member 32 of the type shown in FIG. 8. Each face of the mandrel (only one face visible in FIG. 9) has eight grooves or channels 96 formed therein to form eight pairs of ribs. These channels 96 become filled during the dipping process to form the ribs. As illustrated by the cross-sectional view of FIG. 10 for a single channel pair, each pair of ribs 94 is formed using a pair of overlapping channels 96 that are angularly offset from one another. After the balloon member 32 is removed from mandrel 90', the corresponding ribs 94 are manually glued together. A mandrel that produces non-overlapping ribs can alternatively be used, in which case the proximal and distal walls of the balloon member 32 are squeezed towards one another during the gluing process to cause the ribs to overlap.

Figure 11:
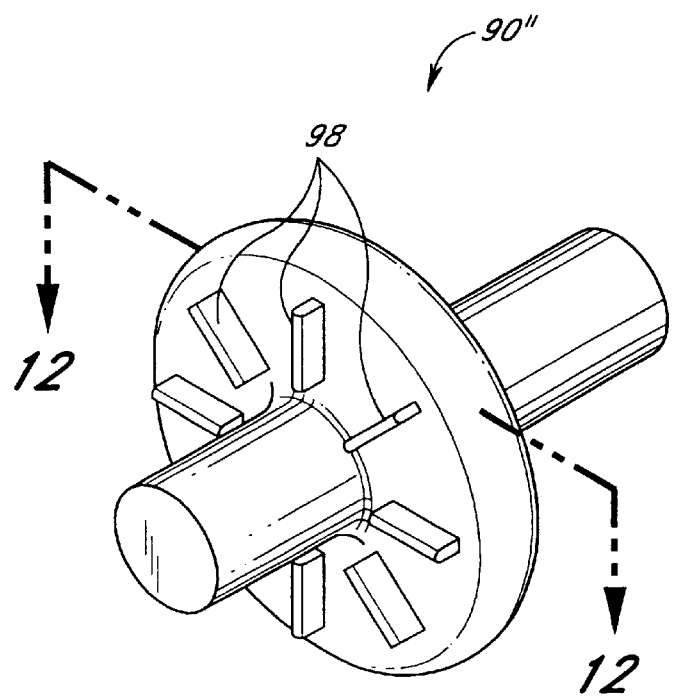
FIG. 11 is a perspective view of another type of mandrel which may be used to generate balloon members of the type shown in FIG. 8.
Figure 12:
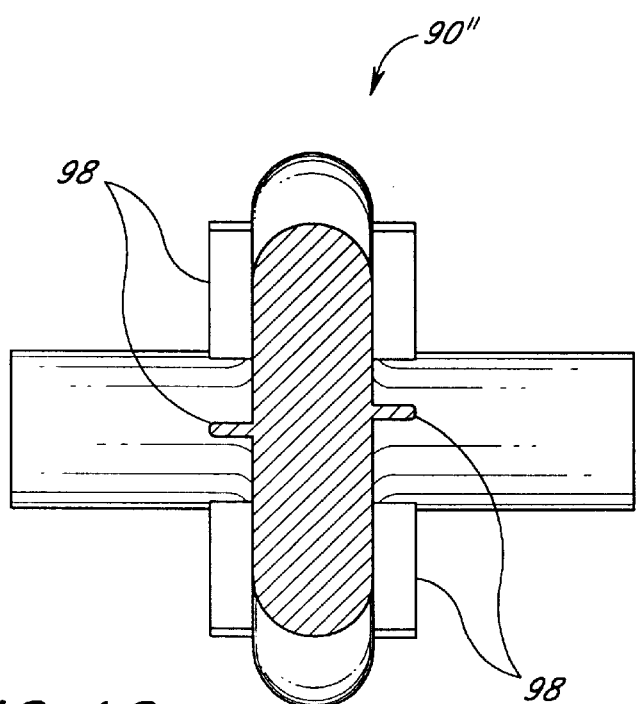
FIG. 12 is a cross sectional view taken along the line 12—12 of FIG. 11.

FIGS. 11 and 12 illustrate an alternative mandrel configuration which can be used to form the ribbed balloon member 32. In this configuration, the channels of the mandrel 90' of FIGS. 9 and 10 are replaced with corresponding protrusions 98 which extend longitudinally outward from each face of the mandrel 90". To form a balloon 36 of the type shown in FIG. 8, the mandrel 90" is initially dipped in a liquid polyethylene, polyurethane or other solution to form a balloon member 32 having ribs which extend outward from the outer surface of the balloon member. This balloon member is then inverted (turned inside out) so that these ribs reside within the balloon member. The corresponding ribs are then glued together, and the inverted balloon member is bonded to the multi-lumen tube 34.

Figure 13A:
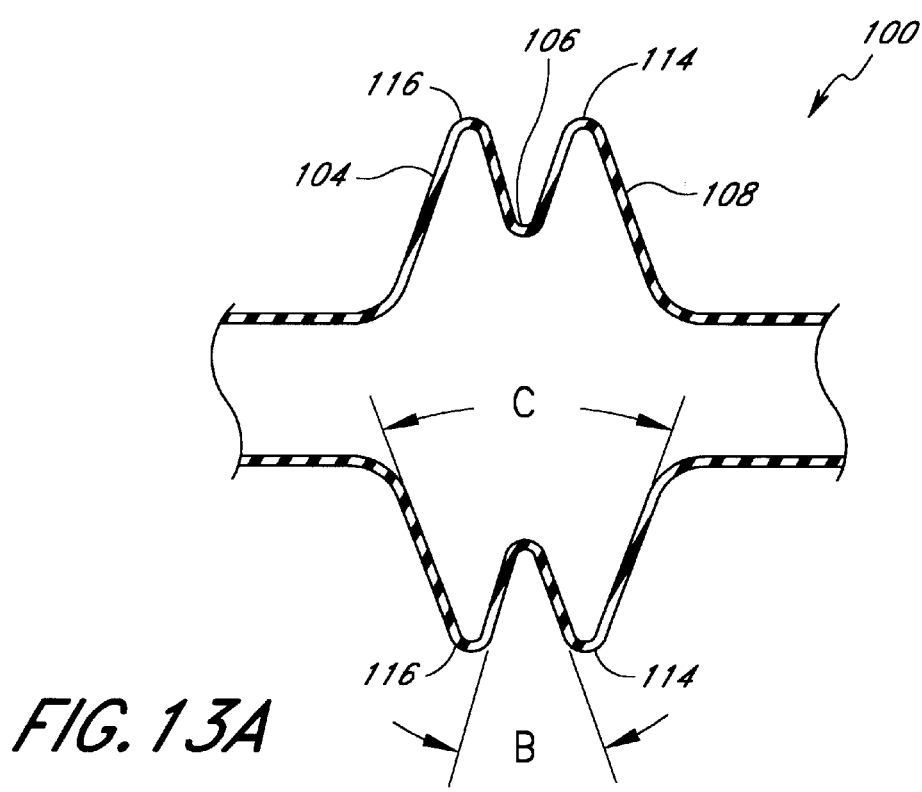
FIGS. 13A and 13B are cross sectional side views of other configurations of the balloon member.
Figure 13B:
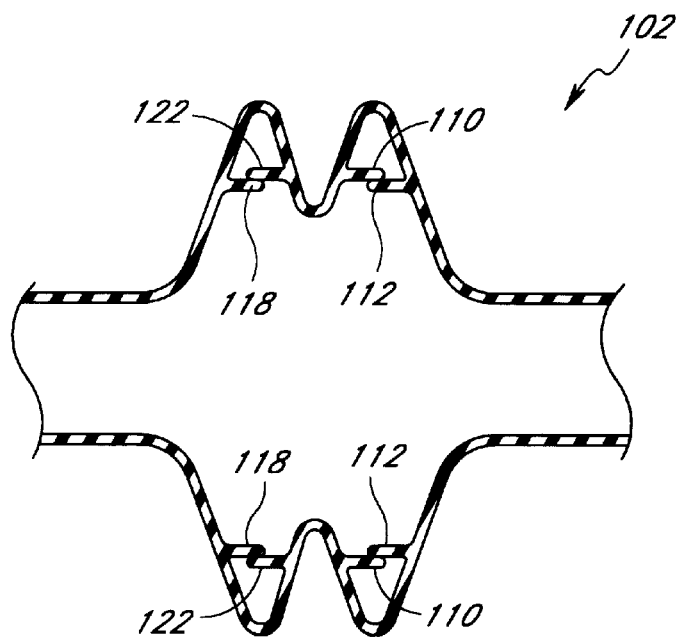

FIGS. 13A and 13B illustrate two alternative configurations of the flexible, inflatable balloon member in accordance with the present invention. The balloon member 100 has a channel, groove or indent 106 formed circumferentially around the balloon's perimeter to form two ridges or peaks 104, 108. This indent 106 may be formed by using a mandrel with a desired indent formed therein. A solvent or adhesive may be applied in the indent 106 to hold the indent 106 in place after the balloon member 100 is removed from the mandrel. Alternatively, the indent 106 may be formed by manually pushing the balloon member 100 inward and applying a solvent or adhesive in the indent 106 to hold the indent 106 in place. The inner edges of the two peaks 104, 108 are held together by the adhesive, but the whole balloon member 100 remains flexible for inflation and deflation. The angle labelled 'B' of the indent 106 is preferably 20 degrees. The angle labelled 'C' of the two peaks 104, 108 is preferably 30 degrees. The configuration in FIG. 13B is similar to the one in FIG. 13A except the peaks contain internal ribs 110, 112, 118, 122 which preferably extend around the circumference of the balloon 102. The configurations in FIG. 13A and 13B are used in generally the same manner as the configurations described above.

The indent in balloons 100, 102 as shown in FIGS. 13A and 13B may extend around the entire peripheral edge of the balloon 100, 102, i.e. 360 degrees. Alternatively, the indent may be provided in select places around the outer peripheral contact area. For example, in one configuration, the indents may be from 30 to 60 degrees, from 120 to 150 degrees, from 210 to 240 degrees, and from 300 to 330 degrees. In other embodiments (not shown), the indents along the outer peripheral contact area are not evenly distributed. For example, the indents may be a series of bumps, zig-zags, or cross-hatches on the outer peripheral contact area. These indents do not divide the outer peripheral contact area into two distinct peaks, but these indents may serve some of the same purposes as the indent and two peaks configuration. Any other indent pattern may be used, such that the pattern preferably does not interfere with occlusion of the blood vessel, i.e. interfere with the seal created by the outer peripheral contact area against the inner wall of the blood vessel. These configurations may be made by a mandrel with a series of bumps, zig-zags or cross-hatches along the peripheral edge.

One purpose for the indent shown in FIGS. 13A and 13B is to hold the balloon member 100, 102 in position within the blood vessel and prevent the balloon member from sliding within the blood vessel. The two peripheral edges provide a better distribution of forces. In other words, when one peak 104 starts to slide, the other peak 108 compensates and holds the balloon member in place. Thus, the two peripheral edge configuration tends to maintain the position of the balloon member within the blood vessel better than a single peripheral edge.

Another purpose of the indent is to maintain the thin profile of the balloon 100, 102. Another purpose is to limit the compliance of the balloon 100. Another purpose is to reduce the surface area of the peripheral edge of the balloon 100, 102 which comes in contact with the internal blood vessel wall. In the embodiments described herein, the peripheral contact area produced by the indented balloon members 100, 102 is less than the contact area produced by the unindented balloon member 32. Reducing the contact surface area reduces the risk of damage to the blood vessel.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed:

1. A device for occluding a patient's blood vessel through direct access of the blood vessel, said device comprising:
   a flexible balloon member having an outer peripheral contact portion for coming in contact with an inner wall of the blood vessel during occlusion, said balloon member being formed of a limited compliance material which limits the expansion of the balloon member to between 1% and 40% radially and between 1% and 50% longitudinally after the balloon member is initially inflated under ambient pressure to its normal, unstretched shape, said balloon member having a diameter, said outer peripheral contact portion being substantially narrower in width than the diameter of the balloon member;
   a tubular member, said balloon member being attached to the tubular member near a distal end of the tubular member, said tubular member comprising:
      a first lumen extending axially within the tubular member, said first lumen adapted to carry blood between the patient and an external medical device; and
      a second lumen extending axially within the tubular member, which conducts fluid to inflate and deflate the balloon member, said second lumen extending to an opening which coincides in position with an interior of the balloon member.

2. The device of claim 1, wherein the balloon member composed of a limited compliance material which limits the expansion of the balloon member to expanding from 1% to 40% radially and from 1% to 50% longitudinally after the balloon member is initially inflated under ambient pressure to itsa normal, unstretched shape.

3. The device of claim 1, wherein the balloon member comprises:
   a first side wall extending between the outer peripheral contact portion and the tubular member;
   a second side wall extending between the outer peripheral contact portion and the tubular member; and
   at least one pair of structure support members extending through a space between the first and second side walls to limit the expansion of the balloon member during inflation.

4. The device of claim 3, wherein the structure support members limit longitudinal expansion of the balloon member.

5. The device of claim 3, wherein the structure support members comprise internal ribs which extend from the first and second side walls.

6. The device of claim 3, wherein the structure support members are formed from the same material as the first and second side walls.

7. The device of claim 3, wherein at least two pairs of structure support members are spaced at equal angular intervals within the balloon member.

8. The device of claim 1, wherein the tubular member has a bend formed therein proximal to the balloon member to facilitate introduction of the balloon member directly into the blood vessel.

9. The device of claim 8, wherein the bend is substantially ninety degrees.

10. The device of claim 1, wherein the balloon member is sized to fit a patient's superior vena cava.

11. The device of claim 1, wherein the tubular member further comprises a blood pressure lumen extending axially within the tubular member, said blood pressure lumen being in fluid communication with a pressure sensor to monitor the blood pressure within the blood vessel.

12. The device of claim 11, wherein the blood pressure lumen and the pressure sensor are used to monitor the blood pressure within the blood vessel proximal to the balloon member.

13. The device of claim 11, wherein the blood pressure lumen and the pressure sensor are used to monitor the blood pressure within the blood vessel distal to the balloon member.

14. The device of claim 1, further comprising an inflation indicating device which indicates when the inflatable balloon is in contact with the inner wall of the blood vessel during occlusion, said inflation indicating device being fluidly coupled to the inflatable balloon.

15. The device of claim 14, wherein the inflation indicating device is a pressure meter which measures the pressure inside the inflatable balloon.

16. The device of claim 1, wherein the balloon member is sized to fit a patient's aorta.

17. The device of claim 1, wherein the expansion of the balloon member is such that its width (L) does not expand to be more than 20% of its diameter (D).

18. The device of claim 1 wherein the balloon member comprises at least one indent along the outer peripheral contact portion which helps the balloon member maintain its position within the blood vessel.

19. The device of claim 18, wherein at least one indent is formed such that the outer peripheral contact portion of the balloon member is divided into at least two peaks.

20. The device of claim 19, wherein each of the two peaks comprises:
a first structure support member on a first internal side wall; and
a second structure support member on a second internal side wall, wherein the first member is attached to the second member.

21. The device of claim 18, wherein at least one indent extends around the entire outer peripheral contact portion of the balloon member.

22. The medical device of claim 1, wherein the limited compliance material limits the expansion of the balloon member to between 10% and 33% radially after the balloon member is initially inflated.

23. The medical device of claim 1, wherein the limited compliance material limits the expansion of the balloon member to between 10% and 40% longitudinally after the balloon member is initially inflated.

24. The medical device of claim 1, wherein the limited compliance material limits the expansion of the balloon member to between 10% and 33% radially and between 10% and 40% longitudinally after the balloon member is initially inflated.

25. The device of claim 1, wherein the expansion of the balloon member is such that its width (L) does not expand to be more than 50% of its diameter (D).

26. A device for occluding a patient's blood vessel through direct access of the blood vessel, said device comprising:
a flexible balloon member having an outer peripheral contact area for coming in contact with an inner wall of the blood vessel during occlusion, said balloon member having a diameter, said outer peripheral contact area being substantially narrower in width than the diameter of the balloon member, said balloon member further comprising at least one pair of internal ribs which interconnect inner walls of the balloon member to limit the expansion of the balloon member during inflation, wherein the internal ribs prevent the balloon member from expanding by more than 10 to 50% longitudinally after the balloon member is initially inflated;
a tubular member which combines with the balloon member to form an inflatable balloon for occluding the blood vessel, said balloon member being attached near a distal end of the tubular member, said tubular member comprising:
a first lumen extending axially within the tubular member, said first lumen adapted to carry blood between the patient and an external medical device; and
a second lumen extending axially within the tubular member, said second lumen adapted to be used to inflate and deflate the balloon member, said second lumen extending to an opening which coincides in position with an interior of the balloon member.

27. A device for occluding a patient's blood vessel through direct access of the blood vessel, said device comprising:
a flexible balloon member having an outer peripheral contact area for coming in contact with an inner wall of the blood vessel during occlusion, said balloon member being formed of a limited compliance material which allows the balloon member to expand between 1% and 40% radially and between 1% and 50% longitudinally after the balloon member is initially inflated under ambient pressure to its normal, unstretched shape, said balloon member having a diameter, said outer peripheral contact area being substantially narrower in width than the diameter of the balloon member;
a tubular member, said balloon member being attached to the tubular member near a distal end of the tubular member, said tubular member comprising:
a first lumen extending axially within the tubular member, said first lumen adapted to carry blood between the patient and an external medical device; and
a second lumen extending axially within the tubular member, which conducts fluid to inflate and deflate the balloon member, said second lumen extending to an opening which coincides in position with an interior of the balloon member; and
an inflation indicating device which indicates when the inflatable balloon is in contact with the inner wall of the blood vessel during occlusion, said inflation indicating device being fluidly coupled to the inflatable balloon, wherein the inflation indicating device is an over-inflation check balloon positioned outside the blood vessel, said over-inflation check balloon inflating when the inflatable balloon is in contact with the inner wall of the blood vessel during occlusion.

28. The device of claim 27, wherein the tubular member has a third lumen formed therein which fluidly connects the balloon member to the over-inflation check balloon.

29. A medical device comprising:
an elongated member having an inflation lumen formed therein; and
an inflatable balloon member attached to the elongated member and fluidly coupled to the inflation lumen, the balloon member comprising:

an outer peripheral contact wall for contacting an inner surface of a blood vessel upon inflation of said balloon member;

a first side wall extending between the outer peripheral wall and the elongated member;

a second side wall extending between the outer peripheral wall and the elongated member; and a plurality of expansion limiting members extending through a space between the first and second side walls, said members attached to said side walls at respective locations spaced radially inwardly from the outer peripheral wall of said balloon member to inhibit separation of said side walls when said balloon member is inflated.

30. The device of claim 29, wherein the elongated member comprises a semi-rigid tube which is adapted to be inserted directly into a blood vessel to be occluded.

31. The device of claim 29, wherein the elongated member comprises a percutaneous catheter.

32. The device of claim 29, wherein the outer peripheral contact wall is substantially narrower in width than the diameter of the balloon member.

33. The device of claim 32, wherein the balloon member comprises at least one indent along the outer peripheral contact wall which helps the balloon member maintain its position within the blood vessel and reduces the surface area of the outer peripheral contact wall contacting the inner wall of the blood vessel.

34. The medical device of claim 29, wherein the members include first and second structure support members which protrude away from said first and second side walls, respectively, and join each other within the interior of said balloon member.

35. A medical device comprising:

an elongated member having an inflation lumen formed therein; and an inflatable balloon member attached to the elongated member and fluidly coupled to the inflation lumen, the balloon member comprising internal ribs which interconnect inner walls of the balloon member to inhibit the overexpansion of the balloon member, wherein the internal ribs prevent the balloon from expanding by more than 50% longitudinally after the balloon is initially inflated.

36. The device of claim 35, wherein the internal ribs prevent the balloon from expanding by more than 10% longitudinally after the balloon is initially inflated.

37. A device for occluding a patient's blood vessel through direct access of the blood vessel, said device comprising:

a flexible balloon member having an outer peripheral contact portion for contacting an inner surface of a wall of the blood vessel, said balloon member being formed of a material that allows said balloon member to stretch radially and longitudinally when inflated, said material having sufficiently limited compliance such that said balloon member maintains its overall shape during said stretching, said balloon member having a diameter (D) which is substantially greater than its length (L) when inflated;

a tubular member having said balloon member thereon, said tubular member sized for introduction through an opening in the wall of the blood vessel and into the vessel such that (i) a distal portion of said tubular member extends from said opening in said vessel wall to said balloon, and (ii) a proximal portion of said tubular member extends out of said opening in said vessel wall, wherein said proximal and said distal portions of said tubular member are both semi-rigid to facilitate such introduction, said tubular member comprising:

a first lumen extending axially within the semi-rigid tubular member, said first lumen adapted to carry blood between the patient and an external medical device; and a second lumen extending axially within the semi-rigid tubular member which conducts fluid for inflating and deflating the balloon member.

38. The device of claim 37, wherein the tubular member has a substantially right angle bend formed therein in the semi-rigid material proximal to the balloon member to facilitate introduction of the balloon member directly into the blood vessel.

39. The device of claim 37, wherein the tubular member comprises a translucent material.

40. The device of claim 37, wherein the expansion of the balloon member is such that its width (L) does not expand to be more than 50% of its diameter (D).

41. The device of claim 37, wherein the expansion of the balloon member is such that its width (L) does not expand to be more than 20% of its diameter (D).

42. A device for occluding a patient's blood vessel through direct access of the blood vessel, said device comprising:

a flexible balloon member having an outer peripheral contact portionf or coming in contact with an inner wall of the blood vessel during occlusion, said balloon member being formed of a limited compliance material which allows the balloon member to expand between 1% and 40% radially and between 1% and 50% longitudinally after the balloon member is initially inflated under ambient pressure to its normal, unstretched shape, said balloon member having a diameter, said outer peripheral contact portion being substantially narrower in width than the diameter of the balloon member; and a tubular member, said balloon member being attached to the tubular member near a distal end of the tubular member, said tubular member comprising:

a first lumen extending axially within the tubular member, said first lumen adapted to carry blood between the patient and an external medical device; and a second lumen extending axially within the tubular member, which conducts fluid to inflate and deflate the balloon member, said second lumen extending to an opening which coincides in position with an interior of the balloon member;

wherein the balloon member comprises:

a first side wall extending between the outer peripheral contact portion and the tubular member;

a second side wall extending between the outer peripheral contact portion and the tubular member; and at least one pair of structure support members extending through a space between the first and second side walls to limit the expansion of the balloon member during inflation, wherein the structure support members are bonded together.

43. A device for occluding a patient's blood vessel through direct access of the blood vessel, said device comprising:

a flexible balloon member having an outer peripheral contact area for coming in contact with an inner wall of the blood vessel during occlusion, said balloon member being formed of a limited compliance material which allows the balloon member to expand between 1% and 40% radially and between 1% and 50% longitudinally after the balloon member is initially inflated under ambient pressure to its normal, unstretched shape, said balloon member having a diameter, said outer peripheral contact area being substantially narrower in width than the diameter of the balloon member;

a tubular member, said balloon member being attached to the tubular member near a distal end of the tubular member, said tubular member comprising:

a first lumen extending axially within the tubular member, said first lumen adapted to carry blood between the patient and an external medical device; and a second lumen extending axially within the tubular member, which conducts fluid to inflate and deflate the balloon member, said second lumen extending to an opening which coincides in position with an interior of the balloon member, wherein the balloon member comprises at least one indent along the outer peripheral contact area which helps the balloon member maintain its position within the blood vessel; and further comprising a solvent in the indent to substantially hold the indent in place after the balloon member is formed.

* * * * *